United States Patent [19]

Makihira et al.

[11] 4,410,278

[45] Oct. 18, 1983

[54] METHOD AND APPARATUS FOR APPEARANCE INSPECTION

[75] Inventors: Hiroshi Makihira; Yasuo Nakagawa; Toshimitsu Hamada, all of Yokohama; Makoto Udaka, Yokosuka, all of Japan

[73] Assignees: Hitachi, Ltd.; Japan Nuclear Fuel Co., Ltd., both of Tokyo, Japan

[21] Appl. No.: 170,181

[22] Filed: Jul. 18, 1980

[30] Foreign Application Priority Data

Jul. 20, 1979 [JP] Japan .................................. 54-91575
Aug. 20, 1979 [JP] Japan ................................ 54-105065
May 16, 1980 [JP] Japan .................................. 55-63943

[51] Int. Cl.³ ...................... G01N 21/55; G01N 21/88
[52] U.S. Cl. ..................................... 356/445; 250/563
[58] Field of Search ................................ 356/445–448, 356/237; 250/562, 572, 224, 223 B; 356/240, 241, 431

[56] References Cited

U.S. PATENT DOCUMENTS

| | | | |
|---|---|---|---|
| 3,427,109 | 2/1969 | Beattie et al. ......................... | 250/224 |
| 4,162,126 | 7/1979 | Nakagawa et al. .................. | 356/237 |
| 4,226,539 | 10/1980 | Nakagawa et al. .................. | 356/445 |
| 4,253,768 | 3/1981 | Yaroshuk et al. .................... | 356/431 |

*Primary Examiner*—Bruce Y. Arnold

*Attorney, Agent, or Firm*—Antonelli, Terry & Wands

[57] ABSTRACT

An apparatus for inspecting the outer peripheral surface of a cylindrical object is disclosed, in which the light in slit form is radiated on the surface of an object such as a nuclear fuel pellet at an angle thereto, the light regularly reflected on the surface is detected by a detector, the detected image signal is quantized at threshold values higher and lower than an average level, and the binary signals are used to detect surface losses separately from an unground part and a metal inclusion as a first detection process. The diffused light is radiated onto the surface of the nuclear fuel pellet at an angle thereto, parallel light rays are radiated onto the surface from the direction perpendicular thereto, the light reflected from the surface of the object is detected by a detector from the direction perpendicular to the surface, the detected image signal is quantized at a threshold level lower than an average level of the image signal for the normal surface, and the binary signal is used to detect, as a second detection process, a crack and a pit separately from a chip, said crack, pit or chip included in surface missing defects detected in said first detection process. The surface defects of the nuclear fuel pellet or the like are thus detected by separating them into at least three types including a chip, an unground part and a metal inclusion, and a crack and a pit.

15 Claims, 24 Drawing Figures

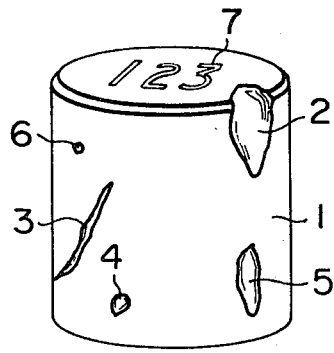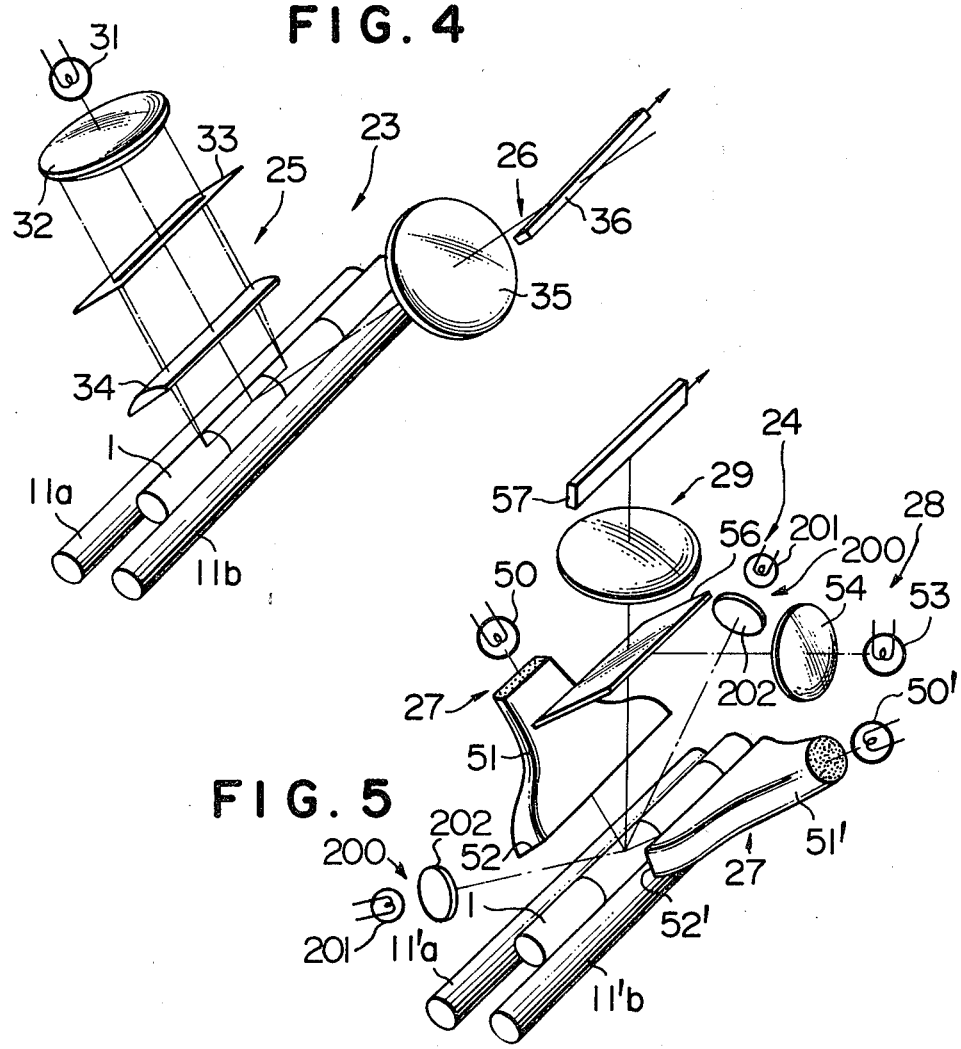

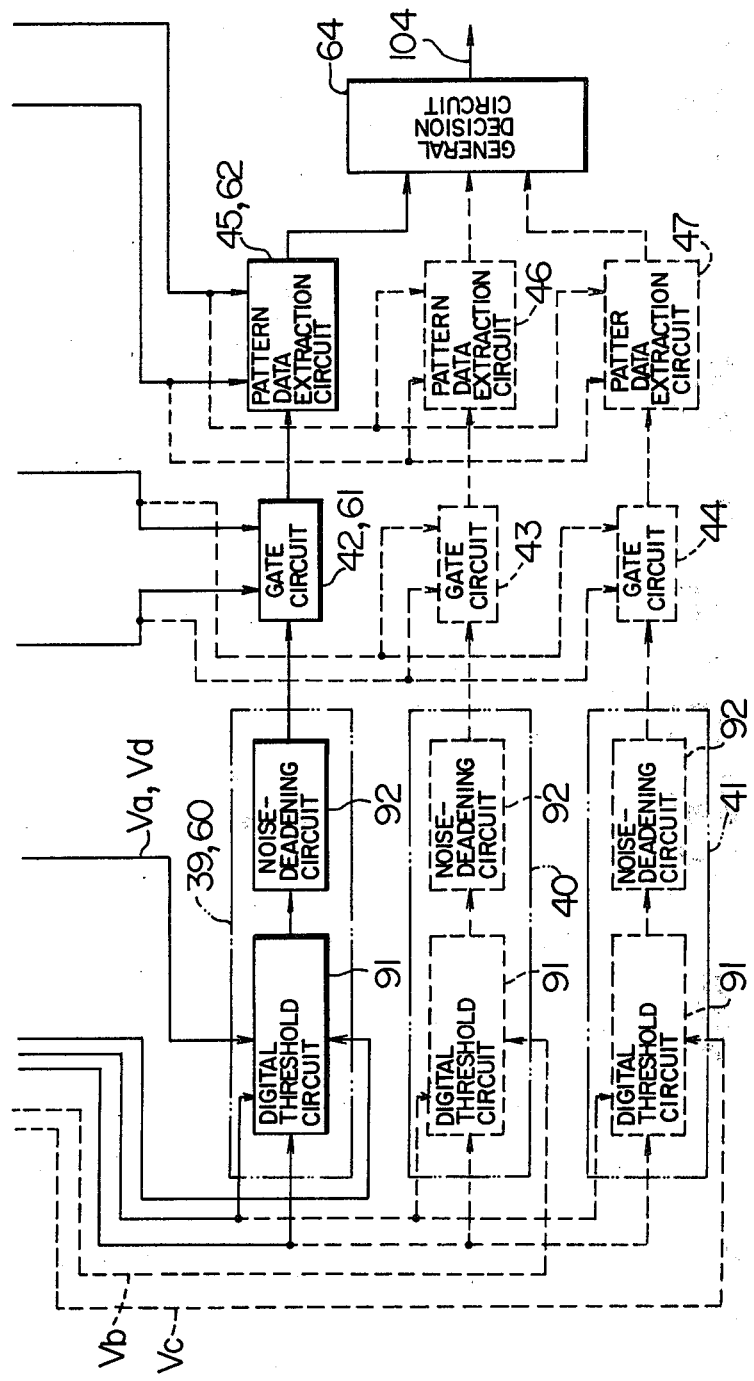

METHOD AND APPARATUS FOR APPEARANCE INSPECTION

The present invention relates to a method and an apparatus for inspecting the external appearance of a solid cylindrical object, or more specifically, to such a method and an apparatus for inspecting a defect such as a chip, a crack or a pit in the outer surface of a solid cylindrical object including uranium and plutonium pellets used as nuclear fuel.

Thermal power generated in a power-generating nuclear reactor is obtained from uranium dioxide pellets in fuel rods installed in the nuclear reactor. Each of the pellets is formed from uranium powder through the steps of pressing, sintering and grinding. In the process of this forming, such defects as a chip 2, an unground part 5, a metal inclusion 6, a crack 3 and a pit 4 occur in the surface of the pellet 1 as shown in FIG. 1. The surface defects such as the chip 2, the unground part 5, the crack 3 and the pit 4 cause the lack of uniformity of heat output or heat conduction. Such defects as the chip 2, the crack 3 and the metal inclusion 6, on the other hand, contribute to mechanical or chemical reaction with the cover tube of the fuel rod, thereby probably adversely affect the performance of the nuclear reactor. In a well-known method of preventing these disadvantages, a total visual inspection is conducted by a human being. In order to improve the efficiency and accuracy of this inspection on the one hand and to reduce the contamination of the operator by radioactivity on the other hand, an attempt was made to establish a method to automatically inspect the defects of the pellet. A prior art apparatus for inspecting the external appearance of solid a cylindrical object is disclosed in U.S. Pat. No. 4,162,126.

The surface of a nuclear fuel pellet has a number of types of defects required to be detected. The criterion for judgement is different for each type of defect. The area is used as a criterion for the chip, width and length for the crack, and the diameter for the pit. Further, a plurality of types of defect may occur at the same part such as a crack within a chip. In other cases, a pit or a crack may occur in or near an identification character 7 including a letter marked as shown in FIG. 1. It is difficult for the abovementioned prior art method and apparatus to inspect by classifying this variety of surface defects regardless of a pattern recognition function added in the stage subsequent to the defect detection.

Other conventional apparatuses for inspection of the outer appearace of a solid cylindrical object are disclosed in Japanese Patent Applications laid-open Nos. 79593/78 and 125057/78 (corresponding to U.S. Pat. No. 4,226,539). A solid cylindrical object is placed on a pair of rollers which are rotated. A plurality of members mounted on a chain conveyor at regular intervals of space and extending upward from between the rollers are brought into contact with the side surface of the cylindrical object which has been fed sequentially to the conveyor. The cylindrical object is moved at predetermined speed along its axis while being rotated around its axis. A stationary optical probe radiates a light ray which illuminates a spot on the outer peripheral surface of the object, and the spot scans spirally around the outer surface of the cylindrical object at a pitch of 1 mm. The light reflected from the outer surface of the object is detected to inspect a chip or other defect. In view of the fact that the object surface is scanned spirally at a pitch as small as 1 mm or less, however, a first disadvantage of this prior art apparatus for automatically inspecting the external appearance of a solid cylindrical object is that inspection of the whole outer surface of an object as long as 10 mm to 15 mm requires 10 to 15 revolutions thereof, resulting in an inefficiently low inspection speed. A second disadvantage of this apparatus is that, in view of the movement of the solid cylindrical object along its axis while being rotated as described above, it is difficult to attain a constant rotational speed of the cylindrical object in a strict sense of the word, thus making it impossible to conduct the inspection with uniformly high accuracy.

In another prior art apparatus intended to overcome this second disadvantage, a multiplicity of solid cylindrical objects are aligned on a pair of rollers in rotation and such objects are rotated at predetermined speed without being moved along the axis thereof. An image pickup device or sensor is comprised of a television camera, a line scanner covering at least a one-dimensional scanning range slightly larger than the length of the solid cylindrical object, and the like. This image sensor is moved intermittently or stepwise along the axis of the object in a manner to cover the length of each cylindrical object, so that the whole outer peripheral surface of the solid cylindrical object is inspected successively by the image sensor in a stationary mode, thus detecting any chips, cracks or like defects. This apparatus is also low in efficiency because the image sensor is moved intermittently in steps corresponding to the length of the cylindrical object.

Accordingly, it is the primary object of the present invention to provide a method and an apparatus for inspecting the external appearance of a solid object such as a nuclear fuel pellet, in which at least one of surface missing defects and convex defects existing in the surface of the object are easily detected.

In order to achieve this object, according to the present invention, light condensed in strip form is radiated at an angle onto the predetermined image sensing area of the surface of said object. The light regularly reflected from the predetermined image sensing area of the surface of the object is picked up by an image sensor, an image signal produced from said image sensor at a threshold level lower than an average level is quantized, and at least one of surface missing defects and convex defects are detected by a binary signal obtained from said quantizing.

Further, the present invention comprises two steps of detection. In the first step of detection, a slit-like light ray is radiated at an angle onto the surface of the object and the light regularly reflected from the surface of the object is detected by an image sensor. The image signal thus detected is quantized by threshold levels which are lower and higher than the average level of image signal associated with a normal surface to obtain binary signals. Each of the binary signals are used to detect the unground part and metal inclusion separately from at least one of surface missing defects such as a chip and convex defects. In the second step of detection, a light ray is radiated at an angle onto the surface of the object, and further, a parallel light ray is radiated onto the surface of the object from a direction perpendicular thereto. The light rays reflected from the surface of the object are detected by an image sensor from the direction perpendicular to the surface of the object. The image signal thus detected is quantized at a threshold level lower than an average level of an image signal associated with a normal surface to obtain a binary signal, and this binary signal is used to detect a crack or a pit separately from the surface missing defects and convex defects detected in the first step of detection. In this way, the surface defects of a cylindrical object are divided into at least three types including a chip, an underground part or metal inclusion, and a crack or a pit for the purpose of detection. Particularly in the first step of detection, an unground part and a metal inclusion are capable of being detected separately by setting two threshold levels higher than an average level of image signal.

Another object of the present invention is to provide an apparatus for inspecting the external appearance of a solid cylindrical object in which an image sensor for one-dimensional scanning inspection is continuously moved along the axis of the cylindrical object thereby to inspect the external peripheral surface of the cylindrical object with high accuracy and without any variation in two-dimensional scanning speed.

According to the present invention, there is provided an apparatus for inspecting the external appearance of a solid cylindrical object, comprising rotary means including at least two rollers for rotating a multiplicity of cylindrical objects at least aligned on the rollers, an image sensor for scaning the outer peripheral surface of the rotating cylindrical object at least one-dimensionally over a range larger than the length of the object and picking up an image therefrom, means for feeding or moving the image sensor continuously in the direction along the axis of the cylindrical object rotated at a predetermined constant speed by the rotating means, means for detecting the speed of movement of the moving means, and means for setting a fixed coordinate of a moving image signal by calculating the amount of movement of an optical image obtained from the outer peripheral surface of the cylindrical object in accordance with the moving speed of the image sensor detected by the moving speed detector means and a predetermined image-forming magnification of the image sensor, wherein the coordinate set by the coordinate setting means is used to process the image signal obtained by the two-dimensional scanning of the image sensor, thus sequentially scanning the outer peripheral surface of the solid cylindrical objects arranged in alignment.

The above and other objects, features and advantages will be made apparent by the detailed description taken in conjunction with the accompanying drawings, in which:

FIG. 1 is a diagram showing the appearance and defective conditions of a nuclear fuel pellet to be inspected by the apparatus according to the present invention;

FIG. 4 is a perspective view showing in an enlarged form a first detector provided at position Q in FIG. 3;

FIG. 5 is a perspective view showing in an enlarged form a second detector provided at position R in FIG. 3;

FIGS. 12A and 12B are a diagram specifically showing the threshold level and coordinate setting circuit shown in FIG. 3;

Figure 2:
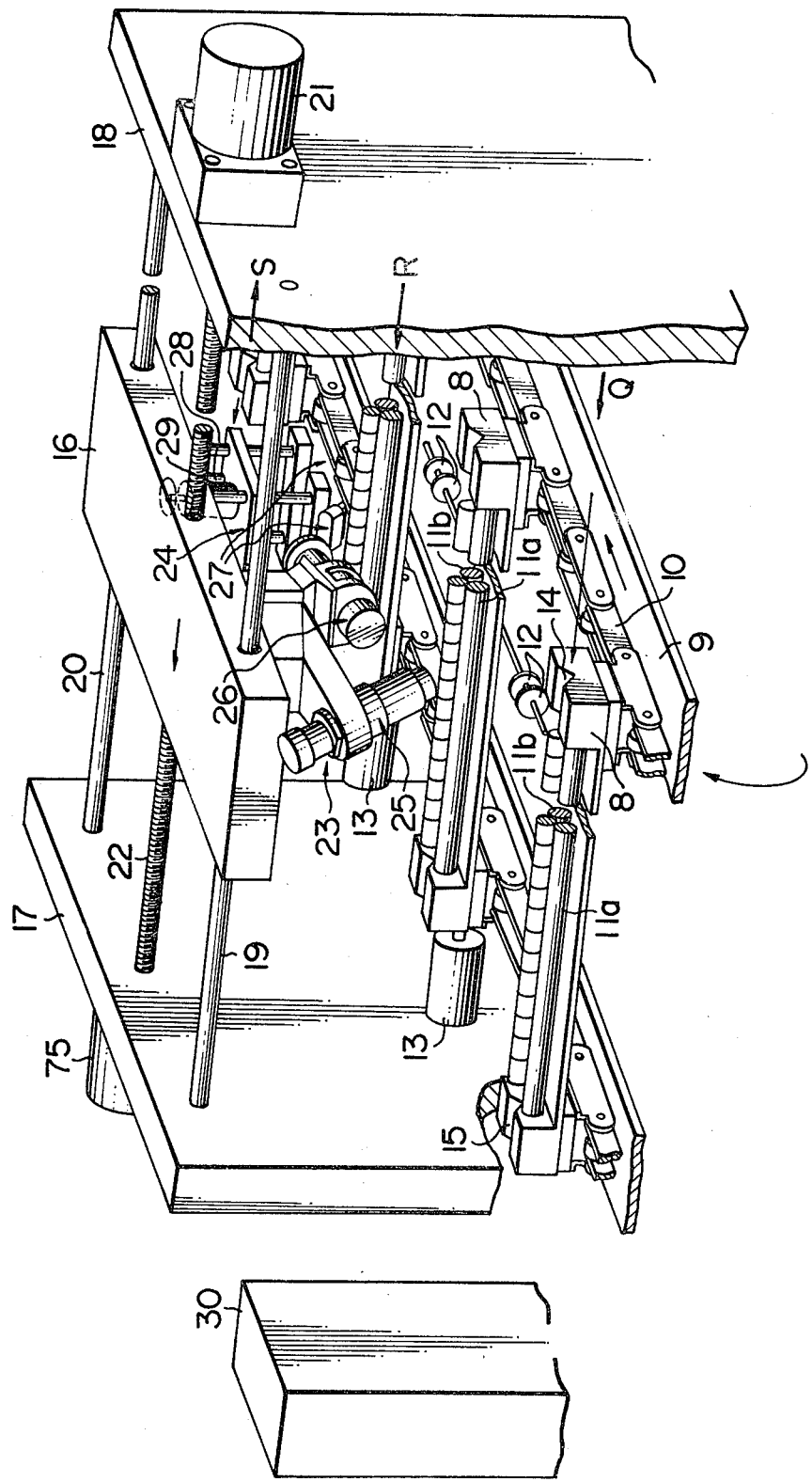
FIG. 2 is a perspective view of an embodiment of the automatic appearance inspection apparatus for a solid cylindrical object according to the present invention.
Figure 3:
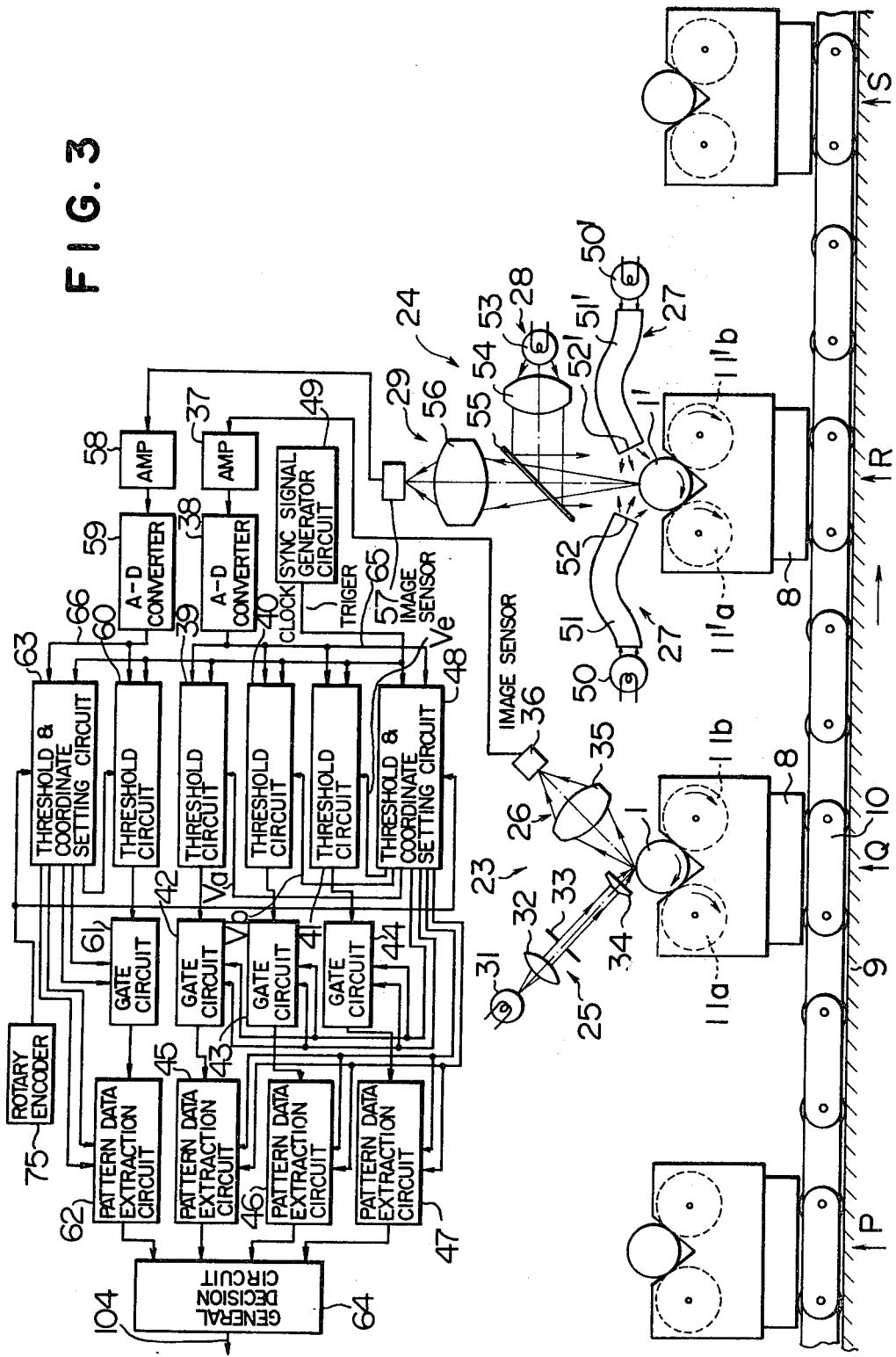
FIG. 3 is a diagram schematically showing the construction of the apparatus of FIG. 2.

An embodiment of the automatic appearance inspection apparatus for a cylindrical object according to the present invention will be described specifically with reference to FIGS. 2 to 9. A perspective view of an embodiment of the automatic appearance inspection apparatus for a cylindrical object according to the present invention is shown in FIG. 2, a schematic construction of the apparatus of FIG. 2 is shown in FIG. 3, a perspective view of a first detector located at position Q is shown in FIG. 3 in enlarged form is shown in FIG. 4, and a perspective view of a second detector located at position R in FIG. 3 in enlarged form is shown in FIG. 5. Reference numeral 1 shows a nuclear fuel pellet of cylindrical form (hereinafter referred to as the pellet). Numeral 8 shows a holding block supported on chain conveyors 10 running on plates 9 on both sides. The holding block 8 rotatably supports rollers 11a and 11b for rotating at a predetermined speed a multiplicity of pellets 1 aligned thereon in contact therewith. These rollers 11a and 11b are coupled to an input shaft (not shown) via a reduction grear or the like (not shown). A pin (not shown) movable laterally in FIG. 2 by a cam follower (not shown) engaged with a rotating cam 12 is fitted and positioned in a positioning hole (not shown) formed in the inner surface of the sides of the holding block 8 when the holding block 8 reaches the positions Q and R. At this time, the output shaft of the motor 13 located at the positions Q and R is coupled with the input shaft mentioned above through a rubber roller or the like. This holding block 8 includes a loading V- groove 14 and an unloading V-groove 15. The loading V-groove 14 enables a multiplicity of pellets to be loaded onto the rollers 11a and 11b along the axis thereof at the loading position P. The unloading V-groove 15, on the other hand, permits the pellets 1 carried on the rollers 11a and 11b and moved in axial direction to be discharged from the rollers 11a and 11b when the chain conveyors 10 are stopped at the unloading position S after completion of the inspection of the outer peripheral surface of the cylindrical objects 1 at the positions Q and R. The holding block 8 is adapted to move intermittently by the chain conveyors 10 and to be positioned and stopped exactly at detecting positions Q and R by a positioning means (not shown). Numeral 16 shows a carriage slidably supported horizontally along guide shafts 19, 20 supported on side frames 17, 18 located at the detecting positions Q and R. This carriage 16 is constructed to engage a feed screw 22 coupled to a driving motor 21 through a reduction gear (not shown). The carriage 16 has a first detector 23 and a second detector 24 on the lower side thereof. The first detector 23 comprises a radiation system 25 for radiating the surface of the pellets in axial linear pattern from the direction at an angle and an image pick-up sensor system 26 for picking up the light reflected from the normal peripheral surface of the pellets from the direction at an angle. The position of the first detector 23 is adjustable. The second detector 24 comprises a first radiation system 27 for radiating the diffused light on the pellets, a second radiation system 28 for radiating the parallel light or diffused light from directly above the pellets, and an image pick-up or sensor system 29 positioned directly above the pellets for picking up the light reflected from the outer peripheral surface of the pellets. The first radiation system 27, the second radiation system 28 and the image pick-up or sensor system 29 are adjustable in height.

At the loading position P, a multiplicity of pellets 1 are supplied and loaded in aligned form from a lateral side through the loading V-groove 14 of the holding block 8 (as described specifically in U.S. Pat. No. 4,226,539. Next, the holding block 8 is moved and stopped alternately at regular predetermined intervals of length so that the holding block 8 is stopped at the detecting positions Q and R sequentially under the carriage 16. Each of the motors 13 is driven to rotate the rollers 11a and 11b at predetermined constant speed thereby to rotate a multiplicity of closely aligned pellets 1 at predetermined speed. When the multiplicity of pellets 1 begin to rotate after the lapse of predetermined length of time following the start of operation, a motor 21 is driven so that the carriage 16 is continuously moved from right to left in FIG. 2 by a feed screw 22. The pellets 1 are rotated by the rollers 11a and 11b without being moved along the axis thereof in order to minimize variations in rotational speed of the pellets 1, thus making it possible for the image sensor systems 26 and 29 to accurately inspect by scanning the outer peripheral surface of the pellets 1 at uniform pitches. Further, in order to greatly improve the efficiency by continuous inspection of the multiplicity of pellets 1, the carriage 16 having the first detector 23 and the second detector 24 are moved continuously along the axis of the pellets 1 as described already.

The above-mentioned first detector 23 for detecting such defects as unground part and a metal inclusion, the second detector 24 for detecting such defects as a crack and a pit and a device 30 for processing signals representing such defects will be described below specifically. As seen from FIG. 3, the radiation system 25 of the first detector 23 comprises a light source 31, a radiation lens 32, a slit 33 with the longitudinal axis thereof directed parallel to the rotating axis of the pellets 1, and a cylindrical lens 34 whereby the light diaphragmed through the slit 33 is condensed linearly along the axis of the pellets on the peripheral surface thereof. In this way, the light condensed in strip form is radiated on the pellets at an angle. The image sensing system 26 of the first detector 23 comprises an image-forming lens 35 for forming a real image of the pellet surface by picking up the light regularly reflected on the pellet surface through the slit, an image sensor 36 including a linear image sensor element of self-scanning type. The image sensor 36 scans the whole of the outer peripheral of the pellet during one revolution thereof. Numeral 37 shows an amplifier circuit for amplifying the image signal produced from the image sensor 36 to a predetermined level. Numeral 38 shows an A-D converter for converting the image signal into a digital image signal by sampling the same with a clock signal. Numerals 39, 40 and 41 show a threshold circuit for quantizing the digital image signal 65 into binary picture elements at a threshold level Va lower than the average level of the normal surface produced from the threshold level setting and coordinate setting circuit 48, a threshold level Vb higher than that and the highest threshold level Vc respectively while at the same time eliminating noises. Numerals 42, 43 and 44 show gate circuits for determining inspection areas ($EG_1+\delta$ to $EG_2-\delta$) for individual pellets. Numeral 45 shows a pattern data extraction circuit for counting the data such as the number of two-dimensional binary patterns (the number of the patterns continuously "1" in two-dimensional fashion) of metal inclusions in the pellet surface from the binary picture element signal obtained from the threshold circuit 39 through the gate circuit 42, thus extracting the data representing the number of metal inclusions having conspicuous characteristics. Numeral 46 shows a pattern data extraction circuit for determining by counting such data as the area of the two-dimensional binary patterns (number of "1" levels) of the unground surface part from the binary picture element signal obtained from the threshold circuit 40 through the gate circuit 43, thus extracting data on the area of the unground surface part having conspicuous characteristics. The pattern data extraction circuit 46 also counts the area of the metal inclusions. In view of the small number of metal inclusions and the small area of each metal inclusion, however, the counting thereof does not affect the general evaluation of the defects and is negligible. Numeral 47 shows a pattern data extraction circuit for determining by counting, for example, the area of the two dimensional binary patterns (number of "1" levels) or chips from the binary picture element signals obtained from the threshold circuit 41 through the gate circuit 44, and thus for extracting data on the area of conspicuous chips. The pattern data extraction circuit 47 also counts the area of cracks and pits. In view of the smallness of the area of cracks and pits as compared with that of chips, however, the general evaluation of defects is not affected. Numeral 40 shows a synchronizing signal generator for producing a pulse signal CLOCK and a scanning sync signal TRIGER.

Numeral 1′ shows a pellet moved to position R by the conveyor 10, and numerals 11a′ and 11b′ show rollers moved to position R by the conveyor 10. The first radiation system 27 of the second detector 24 comprises light sources 50, 50', and light guides 51, 51' of glass fiber with rectangular radiation apertures 52, 52' respectively. The radiation aperatures 52, 52' of the light guides 51, 51' thus make up planner light sources, and radiate the diffused light on the outer peripheral surface of the pellet 1' at an angle from at least two directions symmetric with each other. The second radiation system 28 of the second detector comprises a light source 53, a radiation lens 54 for converting the light into parallel one, and half mirror 54 for reflecting the parallel light from the radiation lens 54 and radiating the same on the pellet 1' at right angle thereto from directly above. A third radiation system 200 of the second detector comprises light sources 201 and colimating lenses 202, and illuminates the pellet from both oblieque directions as shown in FIG. 5. The image sensing system 29 of the second detector 24 comprises an image-forming lens 56 for forming a real image of the surface of the pellet 1' obtained via the half mirror 54, and an image sensor 57 including a linear image sensor element of self-scanning type constructed similarly to the first sensor 36 of the first detector 23. Numeral 58 shows an amplifier circuit for amplifying the image signal produced from the image sensor system 57 up to a predetermined level. Numeral 59 shows an A-D converter circuit for converting the image signal into a digital image signal by sampling the same with clock signals. Numeral 60 shows a threshold circuit for converting the digital image signal 66 into a binary picture element signal at a threshold level Vd lower than the value for the normal surface produced from the threshold level and coordinate setting circuit 63 on the one hand and eliminating noises on the other hand. Numeral 61 shows a gate circuit for determining inspection areas (EG1+δ to EG2−δ) for individual pellets. Numeral 62 shows a pattern data extraction circuit for determining the length Lx along the X axis, the length Ly along the Y axis and the area S of the pit and crack as shown in FIG. 10 from the binary picture element signal obtained from the threshold circuit 60 through the gate 61, so that if the relation $$\frac{Lx \cdot Ly}{S} > \epsilon_1$$

Figure 10A:
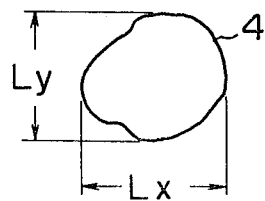
FIG. 10A shows a pit.
Figure 10B:
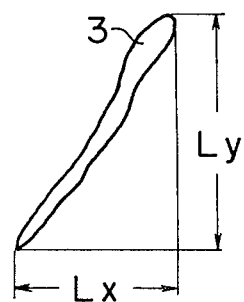
FIGS. 10B and 10C show a crack.

($\epsilon_1$ may take about 1, for instance) is satisfied as shown in FIG. 10B, a crack 3a is identified; if the relation $$\frac{Lx \cdot Ly}{S} > \epsilon_1$$

fails to be satisfied and the relation $$\text{Max}\left(\frac{Ly}{Lx}, \frac{Lx}{Ly}\right) > \epsilon_2$$

Figure 10C:
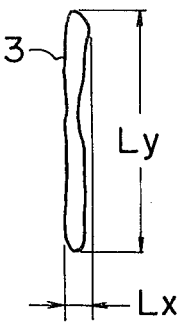

($\epsilon_2$ may take about 1.5, for instance) is satisfied at the same time as shown in FIG. 10C, a crack 3b is identified; and if the relation $$\frac{Lx \cdot Ly}{S} > \epsilon_1 \text{ and Max}\left(\frac{Ly}{Lx}, \frac{Lx}{Ly}\right) > \epsilon_2$$

both fail to be satisfied as shown in FIG. 10A, a pit 4 is identified. In this way, a crack and a pit are distinguished from each other, so that the widths Wx and Wy and the lengths Lx and Ly are determined for the crack, while the diameters Lx, Ly are determined for the pit. Numeral 64 shows a general decision circuit for discriminating the type of defect on the basis of the defect pattern data obtained from the pattern data extraction circuits 45, 46 and 47 and classifying them by comparison with the criterion for each type of defect. Specifically, the general decision circuit 64 operates in such a manner that, for example, the area of the unground surface part 5 obtained from the pattern data extraction circuit 46 is added to the area of the chip 2 obtained from the pattern data extraction circuit 47, the resulting sum of the areas is compared with a criterion, the number of metal inclusions determined by the pattern data extraction circuit 45 is compared with a criterion, the widths Wx, Wy and the lengths Lx, Ly of the crack produced from the pattern data extraction circuit 62 are compared with a criterion, and the pit diameters Lx, Ly obtained from the pattern data extraction circuit 62 are compared with a criterion, thus classifying each pellet 1 and determining whether it is acceptable or rejected.

Figure 6A:
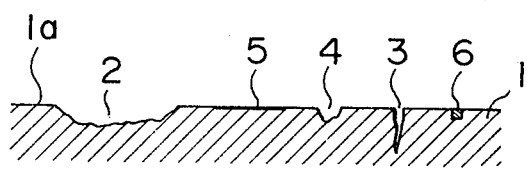
FIG. 6A is a sectional view of a pellet having defects such as a chip, an unground part, a pit, a crack and a metal inclusion in the surface thereof.
Figure 6B:
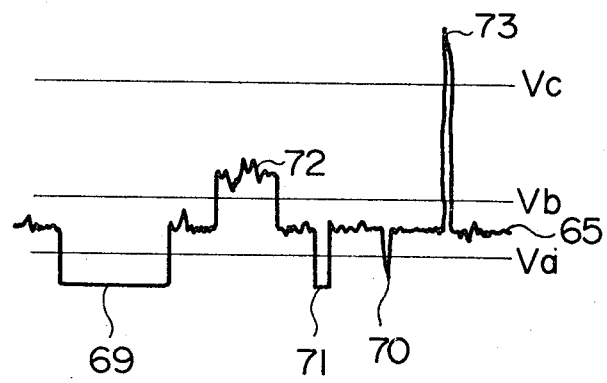
FIG. 6B is a diagram showing threshold levels Va, Vb and Vc and an image signal waveform obtained from the image sensor of the first detector of FIGS. 3 and 4 in accordance with the defects shown in FIG. 6A.
Figure 7:
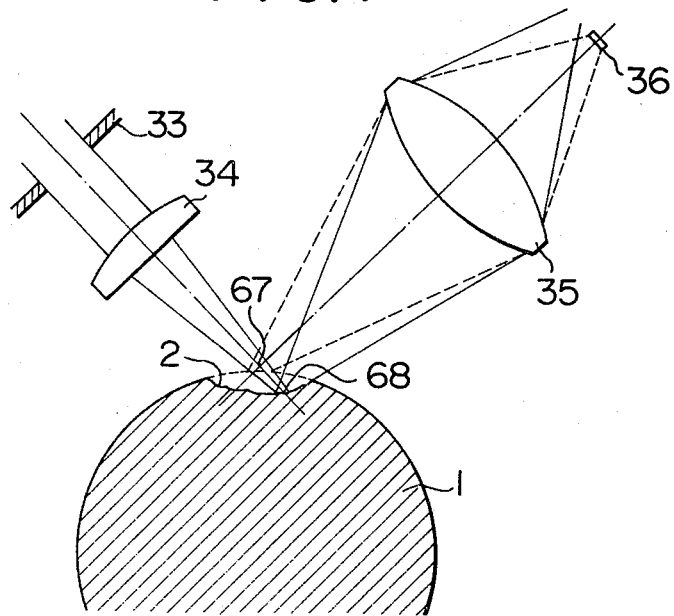
FIG. 7 is a diagram showing the manner in which the light emitted from the first detector shown in FIGS. 3 and 4 is reflected on the pellet surface.

The slit light radiated at position Q in FIG. 3 from the radiation system comprising the light source 31, the radiation lens 32, the slit 33 and the cylindrical lens 34 is diffused on the surface of the pellet 1. Of the diffused light, the regularly reflected light is picked up by the image-forming lens 35 and converted into an electrical signal by the image sensor 36. FIG. 6 shows the relation between the surface condition and the image signal. The pellet surface may be accompanied by such defects as a chip 2 caused by the damage occurred in the process of handling before and after sintering, an unground surface part 5 which is slightly recessed and has failed to be ground, a pit 4 caused by partial removal due to the difference in contraction at the time of sintering, a crack 3 caused by the distortion or the like at the time of forming, and a metal inclusion 6 caused when the surface is ground with a foreign metal mixed therein. FIG. 6A shows an axial sectional view of the peripheral surface of the pellet indicating the chip 2, the unground part 5, the pit 4, the crack 3, and the metal inclusion 6 caused in the surface 1a. FIG. 6B shows an image signal 65 detected by the image sensor 36 at the first position Q. In the presence of the chip 2, the crack 3 or the pit 4, as shown in FIG. 6A, the real image position of the slit which otherwise might be at 67 changes to position 68 as shown in FIG. 7, so that the reflected light fails to enter the linear image sensor 36 as shown by solid line and the image signal 65 represents a dark level as shown by 69, 70 and 71. The unground surface part 5, on the other hand, is the one left sintered which has a lustre unlike the ground normal surface, so that more regularly reflected components are included and the particular part is detected in more bright form as shown by 72. The metal inclusion 6 is a metal surface and therefore is detected most brightly as shown by 73. Therefore, by quantizing at a threshold level Va lower than the normal surface, a threshold level Vb higher than the normal surface and a threshold level Vc highest of all, it is possible to detect the chip 2, pit 4 or crack 3 at the threshold level Va, the unground surface part 5 or metal inclusion 6 at the threshold level Vb, and the metal inclusion 6 at the threshold level Vc. At position Q in FIG. 3, the first detector 23 detects the chip 2, the pit 4 and the crack 3 as a defect collectively and thus is capable of separating them from the unground part 5 and the metal inclusion 6. Incidentally, convex defects may also be detected like the chip 2.

Figure 8A:
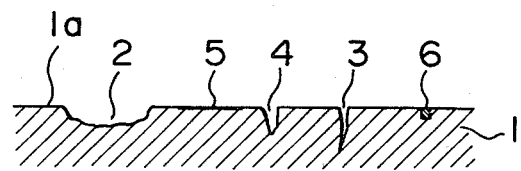
FIG. 8A shows a sectionaly view showing a pellet having such defects in the surface as a chip an unground part, a pit, a crack, and a metal inclusion.
Figure 8B:
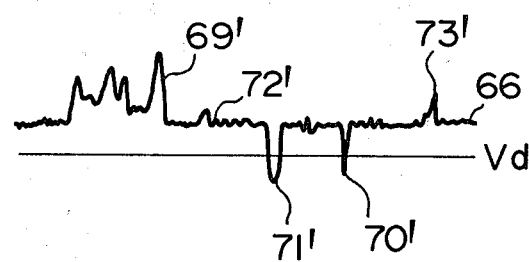
FIG. 8B is a diagram showing a threshold level Vd and an image signal waveform obtained from an image sensor of the second detector shown in FIGS. 3 and 5 in accordance with the defects shown in FIG. 8A.

The light reflected on the radiation device at position R in FIG. 3 which includes the light source 50, the light guide 51, the light source 50', the light guide 51', the light source 53, the radiation lens 54 and the half mirror 55 is diffused on the surface of the pellet 1. The diffused light is picked up at the image-forming lens 56 and converted into an electrical signal by the image sensor 57. FIGS. 8A and 8B show the relation between the surface condition and the image signal in this case. The chip 2 in the pellet surface is of two types including a rough chip caused before sintering and a chip with a smooth conchoidal fractured surface caused after sintering. In view of the fact that the diffused light is radiated at an angle to the surface as shown in FIG. 5, the image derived from the roughness disappears while at the same time increasing the diffused light from the protruded parts, so that the whole of the fractured surface appears bright as shown by 69' in FIG. 8B if the fractured surface is rough. Thus the chip 2 is prevented from being considered to be a pit 4. In the case of a conchoidal smooth fractured surface, on the other hand, the diffused light illumination parts 52 and 52' make up a plane light source, so that the diffused light is partially reflected regularly on the fractured surface, which becomes brighter than the normal surface illuminated at an angle as shown by 69' in FIG. 8B.

In the case of the unground part 5 and the metal inclusion 6, the regularly reflected light obtained from the radiation system comprising the light source 19, the radiation lens 20 and the half mirror 21 enters the image sensor 57. Since the ground surface takes a form similar to frosted glass, it is possible to attain a level equal to or brighter than the normal surface small in regularly reflected components as shown by 72' and 73' in FIG. 8B. Thus only the crack 3 and the pit 4 which are so deep that it is difficult for the illumination light to reach the bottom in spite of wide opening thereof are detected at dark level as shown by 70' and 71' in FIG. 8B. Therefore, by quantizing at the threshold level Vd lower than the normal surface as shown in FIG. 8B, it is possible to detect the crack and pit separately.

Figure 9A:
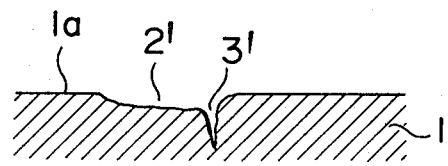
FIG. 9A is a sectional view of a pellet having a crack as a defect.
Figure 9B:
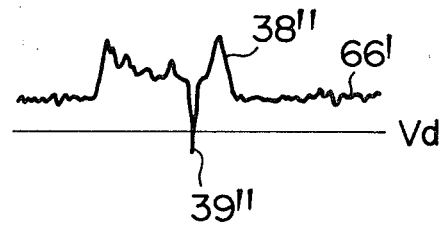
FIG. 9B is a diagram showing a threshold level Vd and an image signal waveform obtained from an image sensor of the second detector of FIGS. 3 and 5 in accordance with the defects shown in FIG. 9A.

In the case where a crack 3' exists in the chip 2' as shown in FIG. 9A, an image signal 66' is detected by the linear image sensor 57 as shown in FIG. 9B. Also in this case, the crack 3' can be detected separately from the chipping 2' by using the threshold level Vd lower than the normal surface. In other words, unlike the linear image sensor 36 at position Q, the linear image sensor 52 at position R is capable of detecting only the pit 4 or crack 3 as separated from the chip 2, so that in combination with the linear image sensor 36 at position Q, the four type of defects including the surface chip 2, the unground part 5, the metal inclusion 6, the pit 4 and the crack 3 are detected separately from each other.

The foregoing description concerns the apparatus for inspection of the peripheral surface. A similar method of detection may be realized for inspection of the ends. In this case, it is very difficult for the prior art to distinguish the printed pattern 7 from the crack 3 as shown in FIG. 1 at the ends. By the detection system at position R in FIG. 3, however, the pit and the crack can be detected separately with high accuracy even if the printed part is too dark to detect or the print coexists with the pit or the crack.

Although the apparatus disclosed above is intended for the detection of the surface defects of a nuclear fuel pellet, the present invention is applicable with equal effect to other objects made of materials such as ceramics, plastics, casting or forging.

As explained above, the first detector 23 positioned at Q is capable of detecting the defects in the surface of an object such as a chip, an unground part and a metal inclusion by distinguishing them from a crack and a pit accurately. By using the detector 23 at position Q in combination with the second detector 24 located at position P, the defects in the surface of an object can be detected by separating them into at least three types: namely, a chip; an unground part or a metal inclusion; and a crack or a pit, thus making possible automatic classification and judgement of the surface defects of a nuclear fuel pellet or the like.

Figure 11:
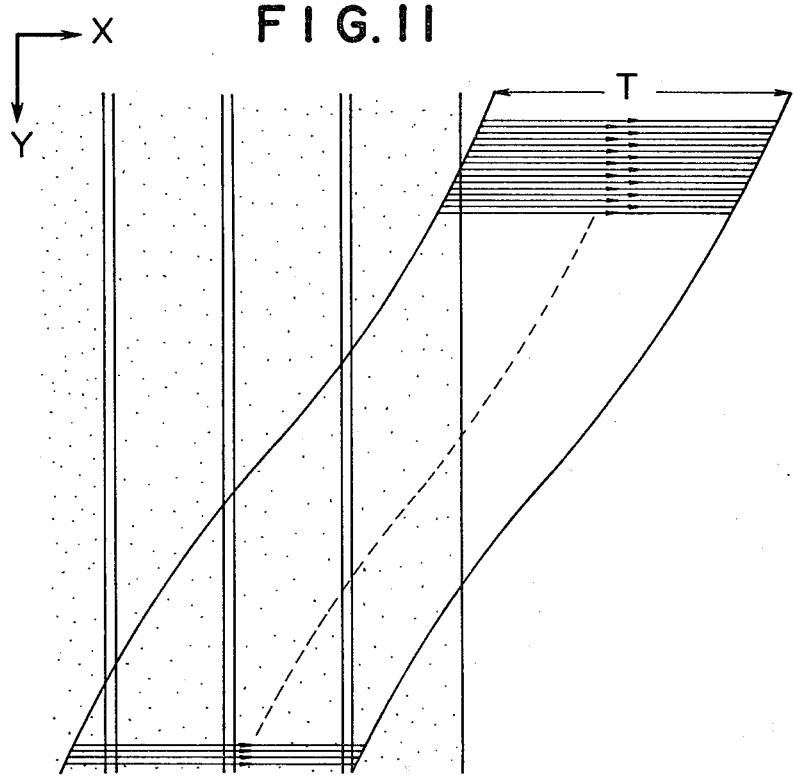
FIG. 11 is a diagram showing a locus of an actual view of field of the image sensor mounted on the carriage shown in FIG. 2.
Figure 12A:
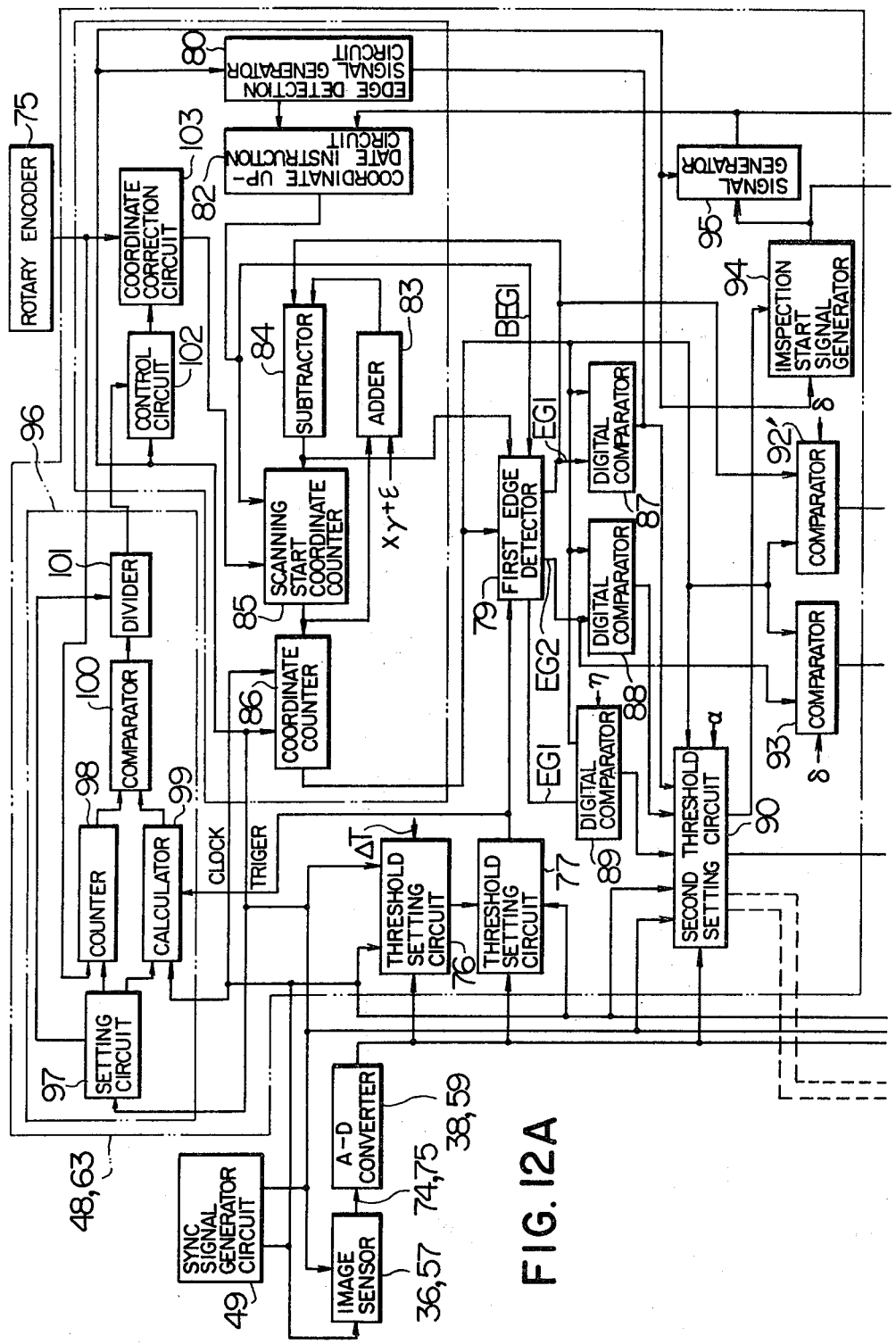

The threshold level and coordinate setting circuit 48, 63 will be described specifically below with reference to FIG. 2 and FIGS. 11 to 15. as described above, in view of the slight variation in the speed of the continuously moved carriage 16, the linear image sensors 36, 57 are operated with the outer peripheral surface pattern of the pellet 1 moved obliquely according to the curved field of view T as shown in FIG. 11. In other words, the linear image sensors 36, 57 repeat the one-dimensional scanning image pick-up operation on the basis of the scanning sync signal TRIGER. The image signals 74, 75 resulting from the one-dimensional scanning pick-up are continuously obtained from the linear image sensors 36, 57.

Numeral 75 shows a rotary encoder coupled to the left end of the feed screw 22 as shown in FIG. 2 for producing a pulse signal each time the carriage 16 is fed by a predetermined length. In other words, the rotary encoder 75 detects the feed rate of the carriage 16. Numeral 46 shows a sync signal generator for generating a scanning sync signal TRIGER and a clock signal. Numerals 38, 59 show an A-D converter circuit for converting image signals 74, 75 into digital signals.

Figure 13A:
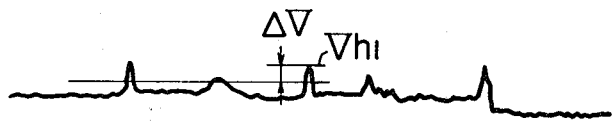
FIGS. 13A, 13B, 13C and 13D show signal waveforms produced from the devices and circuits shown in FIGS. 12A and 12B.
Figure 13B:
Figure 13C:
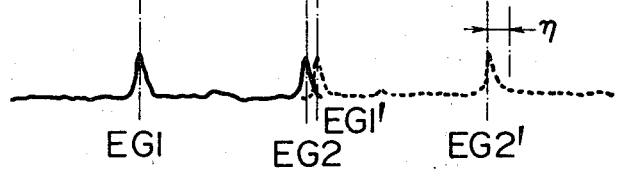
Figure 13D:
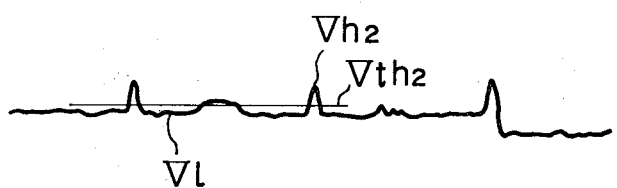
Figure 14:
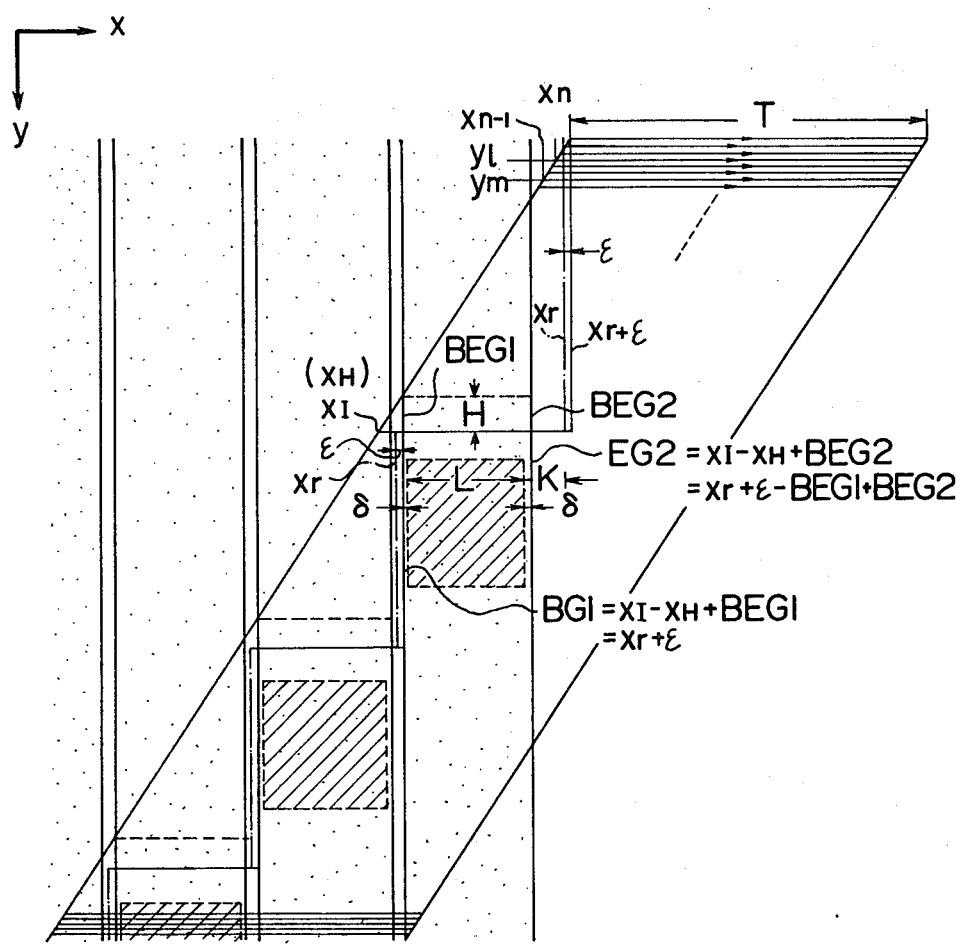
FIG. 14 is a diagram showing the manner in which the start point of scanning by the image sensor mounted on the carriage is shifted and the manner in which the scanning start point is renewed.

The threshold level and coordinate setting circuits 48, 63 will be described specifically. Numeral 76 shows a threshold level setting circuit for edge detection, in which the maximum value Vh of one scanning line of the digital image signal produced from the A-D converter circuit 38, 59 is compared with and reduced by the value ΔV set in a digital comparator in advance, thus setting a first thresold level Vth1 for edge detection. Numeral 22 shows a digital threshold circuit by which the digital image signal produced from the A-D converter circuit 39, 59 at the edge detection threshold level Vth1 set at the first edge detection threshold level setting circuit 26 is converted into a binary picture element. Numeral 78 shows a coordinate control circuit for controlling the coordinate in such a manner that the screen or image picked up by the linear image sensors 36, 57 is kept still on the basis of the pulse signal produced from the rotary encoder 75 and the clock signal and the scanning synch signal TRIGER produced from the sync signal generator 49. This coordinate control circuit 78 comprises an edge detection signal generator circuit 80 for detecting the presence of the first edge position BEG1 upon application thereto of the scanning synch signal TRIGER after detection of the first edge position BEG1 coordinate signal produced from the first edge detector circuit 79, a coordinate update instruction circuit 82 for producing a coordinate update load signal upon production of the first edge position signal from the edge detection signal generator circuit 80 after receipt of an inspection complete signal 81 indicating the completion of inspection of the whole outer peripheral surface of one pellet 1, an adder 83 for adding the coordinate (address) $X_H$ of the extreme left of the field of view before updating as shown in FIG. 14 to the value $(Xr+\epsilon)$, a subtractor 84 for subtracting the first edge position coordinate BEG1 from the output $X_H+(Xr+\epsilon)$ of the adder 83, a scanning start coordinate counter 85 for loading the output of the subtractor 84 and subtracting the same from the pulse produced from the rotary encoder 75 thereby to count the scanning start coordinate (address) at the extreme left of the field of view, and a coordinate counter 86 for receiving a coordinate signal from the scanning start coordinate counter 85, adding the number of clock pulses to the particular coordinate and extracting a coordinate on the scanning line. Numeral 79 shows a first edge detector circuit whereby the binary picture element signal produced from the threshold circuit 77 as shown in FIG. 13B is differentiated to produce a "1" signal at rise and fall points ("0" signals for the other parts), so that a frequency distribution is obtained for, for example, 256 scanning lines as shown in FIG. 13C, which frequency distribution is compared sequentially at a comparator, thus producing a coordinate value (address) of the first maximum edge position BEG1 and the final maximum edge position BEG2. Numeral 87 shows a first digital comparator for producing a signal for starting the extraction of a low-level Vl for determining the second threshold level when the output coordinate of the coordinate counter 86 becomes an updated first edge position coordinate EG1. Numeral 88 shows a final digital comparator for producing a signal for ending the extraction of the low-level Vl while at the same time starting the extraction of the high-level Vh2 when the output coordinate of the coordinate counter 86 becomes an updated edge position coordinate EG2. Numeral 89 shows a digital comparator for producing a signal for ending the extraction of the high-level Vh2 when the coordinate EG1' of the first edge position of the cylindrical object to be updated is attained. Numeral 90 shows a second threshold level setting circuit, whereby on the basis of the signals obtained from the first digital comparator 35 and the final digital comparator 36, as shown in FIG. 13, the digital image signal produced from the A-D converter circuits 38, 59 for, for example, 255 scanning lines over the range from EG1 to EG2 are stored in the addresses of the first memory corresponding to the brightness (output level) thereof thereby to determine the frequency distribution of brightness of the outer peripheral surface of the pellet, the maximum frequency value Vl is determined, and further the digital image signal produced from the A-D converter 23 for 255 scanning lines over the range from EG2 to EG1' as shown in FIG. 13D are stored in the addresses of the second memory corresponding to the brightness thereof (output level), the frequency distribution of brightness is determined for the edge region, and the maximum frequency value Vh2 is obtained, thus setting a threshold level Vth2 represented by $Vth2=\alpha(Vh2-Vl)+Vl$ ($\alpha$ being appropriately changed for Va, Vb, Vc and Vd). The threshold circuits 39, 40, 41 and 60, as mentioned above, comprise a digital threshold circuit 91 for quantizing the digital image signals 65, 66 produced from the A-D converter circuits 38, 59 in response to the second threshold level Va, Vb, Vc and Vd set at the second threshold level setting circuit 90, and a noise deadening circuit 92. Numeral 92' shows a comparator for determining the value $EG1+\delta$ from the signal of EG1 while at the same time producing a "1" signal in the meantime, and numeral 93 shows a comparator for determining the value $EG2-\delta$ from the signal EG2 while at the same time producing a "1" signal in the meantime. Numerals 42, 43, 44 and 61 show gate circuits for passing the range from $EG1+\delta$ to $EG2-\delta$ among the binary picture element signals produced from the noise deadening circuit 92. Numerals 45, 46, 47 and 62 are a pattern data extraction circuit whereby the binary picture element signal that has passed the gate circuit is stored in a memory having, for example, 512 addresses thereby to determine the area, number and the length (width) of the defects. Numeral 64 is a general decision circuit. Numeral 94 shows an inspection start signal generator circuit for producing an inspection start signal in response to a signal with an established second threshold level from the second threshold level setting circuit 90. Numeral 95 shows an inspection end signal generator circuit set by the inspection start signal for generating an inspection end signal when the scanning lines are counted and reach a predetermined number (number for scanning the whole outer periphery of the pellet). Numeral 96 shows an accumulated error measuring circuit comprising a circuit 97 for setting the number of scanning lines, a counter 98, a calculator circuit 99, a comparator 100, and a divider circuit 101. In response to the scanning sync signal TRIGER, the counter 98 counts the pulse signals produced from the rotary encoder 75 from the first scanning line ys to the second scanning line yt with the interval of scanning lines in the number of M set by the setting circuit 97 therebetween. The calculator circuit 99 operates in such a manner that the distance $e_1$, from the binary scanning sync signal TRIGER obtained from the digital threshold circuit 77 at the same first scanning line ys to the first rise is determined by counting the picture elements through the clock pulses, and then the distance $e_2$ from the binary horizontal sync signal obtained from the digital threshold circuit 77 at the second scanning line yt after scanning lines M set by the setting circuit 97 to the first rise is determined by counting the picture elements through clock pulses, so that the difference $e_2-e_1$ is determined. The comparator 100 determines the difference between the value $e_2-e_1$ obtained from the calculator circuit 99 and the value q (corresponding to the target coordinate) obtained at the counter 98. The divider circuit 101 divides the number M of scanning lines set by the setting circuit 97 by the value produced from the comparator 100, and extracts an integral number Ns of scanning lines from the quotient by counting fractions of 0.5 and over as a whole number and disregarding the rest.

Numeral 102 shows a control circuit for operating a coordinate circuit 103 in such a manner that positive and negative signals produced from the divider circuit 101 of the accumulation error measuring circuit 96 and the number Ns of scanning lines are stored, so that upon receipt of a positive signal each time the scanning sync signal TRIGER reaches the number Ns of scanning lines, the last pulse (an integral number of picture elements) of the pulses applied to the coordinate correction circuit 103 from the rotary encoder 75 is eliminated, whereas upon receipt of a negative signal each time the scanning sync signal TRIGER reaches the number Ns of scanning lines, the last pulse (an integral number of picture elements) of the pulses applied to the coordinate correction circuit 103 from the rotary encoder 75 is added.

In the above-mentioned construction, with the aligned pellets 1 rotated at fixed speed by the rollers 11a and 11b as shown in FIG. 2, the illumination light sources 31, 50, 50' and 53 are lit and the motor 21 is started, thus moving the carriage 16 from an end. The linear image sensors 36, 52 are moved together with the carriage 16 in the direction shown by arrow in FIG. 2, while one-dimensionally scanning the surface of the pellets 1 over the range of the field of view S as shown in FIG. 11 thereby to pick up the image of the surface. Thus an image signal is obtained and converted into a digital signal of multiple tone. The scanning start coordinate counter 85 which is initially in preset condition is loaded with $Xr + \epsilon$ set in advance and impressed with pulse signals sequentially from the load encoder 75 with the movement of the image sensors 36, 57, which pulses are subtracted sequentially thereby to store the scanning start coordinate. Thus even if the moving speed of the image sensors 36, 57 are subjected to variations, a rectilinear form is always attained as shown in FIG. 14 by correction by the pulse signal (each one pulse being produced for movement of the linear image sensors 36, 57 by one picture element) produced from the rotary encoder 75. Specifically, as shown in FIG. 14, although the extreme left point of the field of view for the scanning line Yl is $Xn - 1$ in abscissa, the movement of the field of view by one picture element by the scanning start at Ym is detected with the result that the address of the scanning start point of Ym is $Xn - 1$. The coordinate counter 86 is loaded with the scanning start point coordinate Xn stored in the scanning start coordinate counter 85 in response to each scanning sync signal TRIGER, and the counter 86 counts the clock signal from the coordinate Xn thereby to determine the coordinate of each scanning line.

In other words, the value Xr is set in such a manner as to locate the origin along the abscissa to the left out of the field of view of the linear image sensors. Assuming for instance that the linear image sensors have T picture elements in the field of view, the coordinate should be updated or renewed before $Xr + \epsilon$ leaves the field of view at the extreme left thereof initially. For the purpose of this updating, in the absence of the pellet 1 in the field of view, $Xr + \alpha$ is restored to the extreme left point of the field of view when the $X + \epsilon$ is shifted by a predetermined amount from the left end of the field of view. By repeating this process, the image position of the cylindrical object is searched for, and upon detection of the first BEG1 of the pellet 1, Xr is shifted to a nearby position distant by $\epsilon$ therefrom.

In this way, by reading the image signal with the value Xr set in proximity to the image of the pellet 1, it is sufficient for the width of the memory for the particular image data to have only a small margin of width of the maximum image of the pellet to the right of Xr as shown by $\epsilon + L + K$ in FIG. 14.

In other words, the memory has only the width of Xr to $Xr + \epsilon + L + K$. This narrow memory moves and "catches" the image of the pellet each time of the creation thereof to read the data thereon, so that the memory can be used efficiently thus shortening the time required for pattern processing.

The threshold level setting circuit 76 for the first edge detection, on the other hand, searches for a maximum of the digital signals by the digital comparator or the like in a predetermined range of initial change from high to low level, and subtracts $\Delta V$ set in advance from this maximum value Vh thereby to determine the first threshold level Vth1. In response to this first threshold level Vth1 signal, the digital threshold circuit 77 converts the digital image signal into a binary picture element and applies it to the first edge detector circuit 79.

Figure 15:
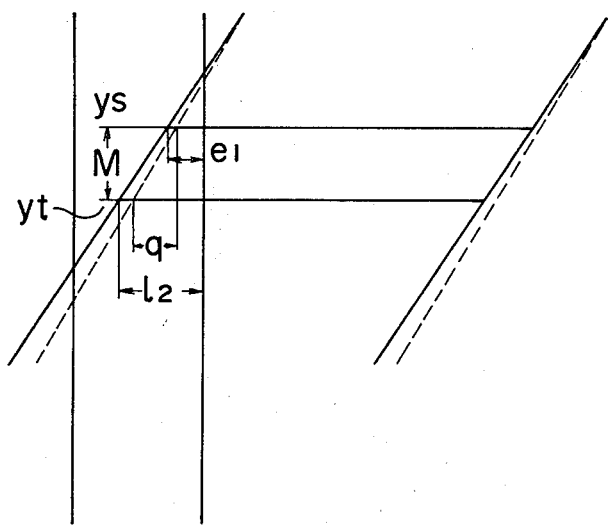
FIG. 15 is a diagram showing an error between the amount of movement of a pattern of the circumferential surface of the pellet and a target coordinate.

As shown by the solid line in FIG. 15, the amount of pattern movement Ls ($= e_2 - e_1$) of the pellet peripheral surface which is determined by the actual amount of movement d of the image sensors 36, 57 and the image forming magnification A has an error with respect to the target coordinate q set while being shifted on the basis of the pulse train signal detected by the rotary encoder 75 shown by the dotted lines in FIG. 15. Prior to inspection, therefore, the number of scanning lines M is set in the setting circuit 97. The calculator circuit 99, in response to a binary picture element signal produced from the digital threshold circuit 77 at the first scanning line Ys, determines the distance $e_1$ to the rise point with reference to the scanning sync signal TRIGER by counting the gated clock pulses with counter of the like. Then, in response to the binary picture element signal produced from the digital threshold circuit 77 at the second scanning line Yk distant by M scanning lines present in the setting circuit 97, the distance $e_2$ to the rise point with reference to the scanning sync signal TRIGER is determined by counting gated clock pulses with counter or the like. The value $e_1$ is subtracted from $e_2$ thereby to determine the amount of pattern movement ($= e_2 - e_1$) of the peripheral surface of the pellet. The counter 98, on the other hand, determines the value q by counting the pulse signals produced from the first scanning line Ys to the second scanning line Yt by the rotary encoder 75. The comparator 100 compares the amount of pattern movement Ls determined by the calculator circuit 99 with the target coordinate shift q determined by the counter 78 thereby to determine the accumulated error at the M scanning lines. The divider circuit 101 determines whether the value Ls/q is positive or negative by calculation thereof on the one hand and an integral number of scanning lines Ns on the other hand. The reason for which the value Ls is divided by the reference amount of coordinate shift q is to determine the number of scanning lines Ns causing an error of one picture element. In order to eliminate the error of one picture element in cycles of Ns scanning lines, the coordinate correction circuit 103 adds one pulse to or eliminate one pulse from the pulse signal produced from the rotary encoder 75 and applies it to the scanning start coordinate counter 85, so that the scanning start coordinate counter 85 corrects the scanning start coordinate (address) at the extreme left of the shifted field of view by one address (on picture element) in cycles of Ns, thus preventing the error from being increased. In this way, prior to the inspection, the data on the surface pattern of the pellet from the first scanning line Ys to the second scanning line Yt is taken in, and the number of scanning lines Ns determined at the accumulated error measuring circuit 96 is stored in the control circuit 102. As a result, as the image sensors 36, 57 are moved from right to left as viewed in FIG. 2 while sequentially taking pictures of the pellets 1 aligned with each other, the shift error is corrected in cycles of Ns thereby to enable the solid line to substantially coincide with the dotted line in FIG. 15. Although it was explained above that the pattern always coincides with the target coordinate in the absence of a shift error, it is difficult as a matter of fact to enable the shift timing for them to coincide with each other, unavoidably resulting in the lack of coincidence by about ±1 picture element.

The first edge detector circuit 79 differentiates the binary picture element signal, the result thereof being stored in a fall counter for falls and a rise counter for rises, which are counted to determine the frequency distribution for, for example, H (=256) scanning lines from the time when the picture element signal begins to include the rise BEG1 of edge. The fall frequency distribution stored in the fall counter is read out for the range from the first address to a predetermined address $Xr+\epsilon+L/2$, and after sequential comparisons at a comparator, an address representing the maximum (initial edge position coordinate BEG1) is produced. Also, the rise frequency distribution stored in the rise counter is read for the range from the address $Xr+\epsilon+L/2$ to the address $Xr+\epsilon+3/2L$, and after sequential comparison at a comparator, an address associated with the maximum (the final edge position coordinate BEG2) is produced. When the coordinate value produced from the coordinate counter 86 reaches this coordinate value of BEG1, the comparator 87 is actuated so as to actuate the edge detection signal generator circuit 80. As a result, a coordinate update load signal is produced from the coordinate update instruction circuit 82 together with the scanning sync signal TRIGER. The coordinate value $X_H$ produced from the scanning start coordinate counter 85 is added to $Xr+\epsilon$ at the adder 83, while the subtractor 84 subtracts BEG1, thus updating the data in the scanning start coordinate counter 85 to the value $X_I=(X_H+Xr+\epsilon-BEG1)$. This is derived from the relation that $X_I-Xr=X_H-(BEG1-\epsilon)$. Then the initial value of the coordinate counter 86 is also updated, and so is the address of the first edge detector circuit 79. In response to the signals EG1, EG2 and EG1' produced in updated form from the comparators 87, 88 and 89, the second threshold level setting circuit 90 determines the frequency distribution by storage at the address of the memory corresponding to the brightness level of the digital image signal from EG1 to EG2 thereby to search for the brightness level Ve representing the maximum value. In similar fashion, the second threshold level setting circuit 90 determines the frequency distribution by storage at the address of another memory corresponding to the brightness level of the digital image signal in the range from EG2 to EG1' (Search is made for a predetermined range set from EG2 initially when EG1' fails to be extracted) thereby to search for the brightness level Vh2 representing the maximum value, so that the calculation of Vth2=α(-Ve−Vh2)+Vh2 is performed thus setting the second threshold level Vth2 (Va, Vb, Vc and Vd). The digital image signal is converted into binary picture elements at the second threshold levels Va, Vb, Vc and Vd and is comprised of picture elements arranged 3 by 3, noises of which are eliminated by a noise deadening circuit 92 taking a logic product of all the picture elements. These binary picture element signals are passsed through the gate circuits 42, 43, 44 and 61 between the signals EG1+δ and EG2−δ produced by the comparators 92, 93 and applied to the pattern data extraction circuits 45, 46, 47 and 62. The pattern data extraction circuits 45, 46, 47 and 62 count the number of picture elements representing defects thereby to determine the size of the defects over the whole surface, to determine the number of such defects or to determine the width, length or diameter of the defects as shown in FIG. 10, thus identifying the conditions of the defects, during the period from receipt of the inspection start signal from the inspection start signal generator circuit 94 to the receipt of an inspection end signal from the inspection end signal generator circuit 95. The general decision circuit 64 decides whether the result of inspection is acceptable or to be rejected, and produces a signal 104 representing the result of inspection. In this way, while correcting the variation in the moving speed of the image sensors 36, 57 at each moment, the coordinate to be stored in the memory as to the image signal following the movement of the image sensors 36, 57 is shifted while at the same time updating the coordinate stored in the memory for each pellet. Thus the linear image sensors 36, 57 are always capable of picking up the image from the whole outer peripheral surface of each pellet as if it is stationary in relation to the pellet 3, thus making possible accurate and efficient inspection of the external appearance of the pellets.

In particular, a multiplicity of aligned pellets are revolved at predetermined speed by rollers to enable the scanning of the whole outer peripheral surface thereof at uniform pitches, without sliding the pellets along the axis of the rollers. Instead, the image sensors are moved continuously along the axis of the pellets for the purpose of inspection of the whole outer peripheral surface of the aligned pellets.

It will be understood from the foregoing description that according to the second detector of the present invention, the defects in the pellet surface such as a chipping, an unground part and a metal inclusion can be detected accurately separately from such defects as a crack and a pit. Also, by providing two threshold levels Va and Vb for the first detector according to the present invention, the pellet surface defects such as an unground part and a metal inclusion can be detected separately from a crack, a chipping and a pit accurately. Further, by using the first detector in combination with the second detector according to the present invention, at least three forms of pellet surface defects of a chipping, an unground part or a metal inclusion, and a crack or a pit can be detected separately, thus making possible automatic classification and judgement of the surface defects of a nuclear fuel pellet or the like.

According to the present invention, a multiplicity of pellets or cylindrical objects are aligned on rollers rotated at predetermined fixed speed, image sensors are moved continuously along the direction of alignment of the cylindrical objects, the amount of movement (speed) of the image sensors is detected, the picture element coordinate of the image signal produced from the images sensors following the movement thereof is corrected and shifted from time to time to prevent any accumulated error, and further the coordinate is updated for each one or two cylindrical objects. As a result, as compared with the conventional apparatus in which the image sensors are intermittently fed to pick up the image of the object surface in stationary form along, the present invention has a conspicuous advantage that the outer peripheral surface of a multiplicity of aligned cylindrical objects is inspected both efficiently and accurately with a minimum memory.

What is claimed is:

1. A method of inspecting the appearance of the outer surface of an object comprising:
   a first detection process including steps of
   (a) radiating light condensed in strip form into a predetermined area and from a direction at a non-zero angle to the normal to the surface of the object,
   (b) picking up by an image sensor the light regularly reflected from the surface of the object, (c) quantizing an image signal produced from said image sensor at least at two threshold levels, one higher and one lower than the average signal level produced by said image sensor, and providing binary signals having values in accordance therewith, and (d) detecting defects in the surface of the object including at least one of an unground part and a metal inclusion separately from at least one of surface missing defects and convex defects by the values of said binary signals produced by the quantization, and a second detection process including steps of (a) radiating light onto a predetermined image sensing area of the surface of an object, from a plurality of directions, (b) picking up by an image sensor the light reflected from the predetermined area in the direction perpendicular to the surface of the object, (c) quantizing an image signal produced from said image sensor at a threshold level lower than the average signal level produced by said image sensor and providing a binary signal having a value in accordance therewith, and (d) detecting the presence of at least one of a crack and a pit in the surface of said object by the value of said binary signal produced by the quantization.

2. A method of the appearance of the outer surface of an object according to claim 1, wherein the image sensor of the first and second detection process scans the surface of the object.

3. An apparatus for inspecting the appearance of the outer surface of an object, comprising:

(A) a first detector including
  (a) first means for radiating light condensed in strip form on a predetermined image sensing area of the surface of the object at an angle thereto,
  (b) first image sensing means for picking up the light reflected regularly from the predetermined image sensing area of the surface of the object radiated by said first radiating means, said first image sensing means scanning said surface two-dimensionally,
  (c) a plurality of threshold circuits for quantizing an image signal produced from said first image sensing means at least at two threshold values one lower and one higher than the average signal level provided by said first image sensing means and providing binary signals having values in accordance therewith, and
  (d) means for detecting the presence of surface defects including at least one of an unground part and a metal inclusion separately from at least one of surface missing defects and convex detects by the values of said binary signals produced from said threshold circuits, said first detector being located at a first position, and (B) a second detector including
  (a) second means for radiating light onto a predetermined image sensing area of the surface of the object from a plurality of directions,
  (b) second image sensing means for picking up the light radiated by said second radiating means and reflected from the predetermined image sensing area in the direction perpendicular to the surface of the object, said second image sensing means scanning the surface of said object two-dimensionally,
  (c) a threshold circuit for quantizing an image signal produced from said second image sensing means at a threshold value lower than the average signal level and producing a binary signal having a value in accordance therewith, and
  (d) means for detecting the presence of defects including at least one of a crack and a pit in the surface of the object by the value of said binary signal produced from said threshold circuit, said second detector being located at a second position; and (C) carriage means for carrying said object from one of said first and second positions to the other position.

4. An apparatus for inspecting the appearance of the outer surface of an object according to claim 3, wherein said second radiating means includes one radiating means for radiating the light on a longitudinal image sensing area at an angle from both directions and another radiating means for radiating the light from the direction perpendicular to the surface of the object.

5. An apparatus for inspecting the appearance of the outer surface of an object according to claim 3, wherein said carriage means further includes rotary means having at least two rollers for carrying and at least aligning a multiplicity of cylindrical objects in contact therewith, said rotary means rotating said cylindrical objects on the axis thereof at a predetermined speed, said rotary means being juxtaposed in the direction of carriage in a plurality of number.

6. An apparatus for inspecting the appearance of the outer surface of an object according to claim 3, wherein each of said first and second detectors further comprise:

rotary means including at least two rollers for at least aligning a multiplicity of cylindrical objects on said rollers in contact therewith and rotating said cylindrical objects on the axis thereof at a predetermined speed, another carriage means for carrying and moving said radiating means and said image sensing means along the axis of the cylindrical objects, means for detecting the moving speed of said another carriage means, means for setting a coordinate in accordance with the moving speed of said image sensing means detected by said moving speed detecting means and a predetermined image-forming magnification of said image sensing means, and means for sequentially inspecting the outer peripheral surface of said cylindrical object on the basis of the coordinate set by said coordinate setting means, said detector means processing the binary signal produced from said threshold circuit.

7. An apparatus for inspecting the appearance of the outer surface of an object according to claim 3, further comprising:

rotary means including at least two rollers for at least aligning a multiplicity of cylindrical objects on said rollers in contact therewith and rotating said cylindrical objects on the axis thereof at a predetermined speed, another carriage means for carrying and moving said radiating means and said image sensing means along the axis of the cylindrical objects, means for detecting the moving speed of said another carriage means, coordinate setting means for measuring the number of scanning lines required for an integral number of picture elements to represent the area between a target coordinate determined in advance by the amount of movement detected by said moving speed detecting means and the amount of movement of a pattern of the outer peripheral surface covered by said image sensing means, a threshold circuit for converting into a binary picture element an image signal produced from said image sensing means by two-dimensional scanning, and means for processing the binary picture element signal produced from said threshold circuit on the basis of the coordinate set by said coordinate setting means, thereby sequentially scanning the outer peripheral surface of the aligned cylindrical objects.

8. An apparatus for inspecting the appearance of the outer surface of an object according to claim 3, wherein each of said first and second image sensing means comprises an image sensing device including an image-forming lens and a linear image sensor.

9. An apparatus for inspecting the appearance of the outer surface of an object according to claim 3, wherein said first radiating means includes a light source, a slit for shaping light from said light source, and a cylindrical lens for condensing the light in strip form.

10. An apparatus for inspecting the appearance of the outer surface of an object according to claim 9, wherein each of said first and second image sensing means comprises an image sensing device including an image forming lens and a linear image sensor.

11. An apparatus for inspecting the appearance of the outer surface of an object according to claim 9, wherein each of said first and second image sensing means comprises an image sensing device including an image forming lens and a linear image sensor.

12. An apparatus for inspecting the appearance of the outer surface of an object, comprising rotary means having at least two rollers for carrying and at least aligning a multiplicity of cylindrical objects in contact therewith, said rotary means rotating said cylindrical objects on the axis thereof at a predetermined speed, image sensing means for scanning and picking up an image at least one-dimensionally from the outer peripheral surface of said cylindrical objects along the axis thereof over an area wider than the length of said cylindrical object rotated by said rotary means, moving means for moving said image sensing means, means for detecting the moving speed of said moving means, and means for setting a coordinate in accordance with the moving speed detected by said moving speed detecting means and a predetermined image-forming magnification of said image sensing means, said apparatus further comprising means for processing an image signal obtained by two-dimensional scanning of said object from said image sensing means on the basis of the coordinate set by said coordinate setting means, thereby sequentially inspecting the outer peripheral surface of said aligned cylindrical objects.

13. An apparatus for inspecting the appearance of the outer surface of an object according to claim 12, wherein the scanning image sensing of said image sensing means is at least twice the length of said cylindrical object.

14. An apparatus for inspecting the appearance of the outer surface of an object, comprising: rotary means, including at least two rollers, for carrying and at least aligning a multiplicity of cylindrical objects in contact therewith, said rotary means rotating said cylindrical objects on the axis thereof at a predetermined speed; image sensing means for scanning, at least one-dimensionally, and picking up an image from the outer peripheral surface of said cylindrical objects over an area wider than the length of said cylindrical object, said cylindrical objects being rotated by said rotary means; moving means for moving said image sensing means; movement amount detection means for detecting the amount of movement of said moving means; coordinate setting means for measuring the number of scanning lines required for an integral number of picture elements to represent the error between a target coordinate determined in advance by the amount of movement detected by said movement amount detecting means and the amount of movement of a pattern of the outer peripheral surface covered by said image sensing means; said coordinate setting means correcting said target coordinate by said integral number of picture elements each time of covering said scanning lines by said image sensing means; and a threshold circuit for converting into a binary picture element an image signal produced from said image sensing means said apparatus further comprising means for processing the binary picture element signal produced from said threshold circuit on the basis of the coordinate set by said coordinate setting means, thereby sequentially scanning the outer peripheral surface of said aligned cylindrical objects.

15. An apparatus for inspecting the appearance of the outer surface of an object, comprising:
 (a) a first detector including
   (a) means for radiating light condensed in strip form on a predetermined image sensing area of the surface of the object at a non-zero angle thereto,
   (b) first image sensing means for picking up the light reflected regularly from the predetermined image sensing area of the surface of the object radiated by said radiating means, said first image sensing means scanning the surface of the object two-dimensionally,
   (c) a threshold circuit for quantizing an image signal produced from said first image sensing means at least at one threshold value lower than the average signal level produced by said first image sensing means and providing a binary signal having a value in accordance therewith, and
   (d) means for detecting the presence of surface defects including at least one of surface missing defects and convex defects by the value of said binary signal produced from said threshold circuit, said first detector being located at a first position, and
 (B) a second detector including
   (a) radiating means for radiating light into a predetermined image sensing area of the surface of the object from a plurality of directions,
   (b) second image sensing means for picking up the light radiated by said radiating means and reflected from the predetermined image sensing area in the direction perpendicular to said surface of the object, said second image sensing means scanning the surface of said object two-dimensionally,
   (c) a threshold circuit for quantiizing an image signal produced from said image sensing means at a threshold value lower than the average signal level produced by said second image sensing means and providing a binary signal having a value in accordance therewith, and (d) means for detecting the presence of defects including at least one of a crack and a pit in the surface of the object by the value of said binary signal produced from said threshold circuit, said second detector being located at a second position; and (C) carriage means for carrying said object from one of said first and second positions to the other position.

* * * * *